United States Patent [19]

Bolze et al.

[11] Patent Number: 4,518,801
[45] Date of Patent: May 21, 1985

[54] PROCESS FOR THE HYDROLYSIS OF 5-(β-METHYLMERCAPTOETHYL)-HYDANTOIN

[76] Inventors: Rudolf Bolze, Grünaustrasse 11, 6450 Hanau 9; Friedhelm Geiger, Kurt-Schumacher-Strasse 30 a, 6455 Erlensee; Manfred Spindler, Kurfurstenstrasse 24, 6450 Hanau 1; Herbert Tanner, Wildaustrasse 20, 6450 Hanau 9, all of Fed. Rep. of Germany

[21] Appl. No.: 648,136

[22] Filed: Sep. 7, 1984

[30] Foreign Application Priority Data

Sep. 29, 1983 [DE] Fed. Rep. of Germany ....... 3335218

[51] Int. Cl.³ .......................................... C07C 149/247
[52] U.S. Cl. ..................................................... 562/559
[58] Field of Search ......................................... 562/559

[56] References Cited

U.S. PATENT DOCUMENTS

| | | | |
|---|---|---|---|
| 2,527,366 | 10/1950 | Livak | 562/559 |
| 2,557,913 | 6/1951 | Livak | 562/559 |
| 2,557,920 | 6/1951 | White | 562/559 |
| 3,636,098 | 6/1967 | Shima | 562/559 |
| 3,668,221 | 6/1972 | Shima | 562/559 |
| 3,790,599 | 2/1974 | Zundel | 562/559 |
| 3,833,651 | 9/1974 | Ouchi | 562/559 |
| 4,069,251 | 1/1978 | Mannsfeld | 562/559 |
| 4,272,631 | 6/1981 | Schaaf | 562/559 |
| 4,436,910 | 3/1984 | Kleemann | 562/575 |

Primary Examiner—Michael L. Shippen
Attorney, Agent, or Firm—Cushman, Darby & Cushman

[57] ABSTRACT

The invention is directed to a process for the hydrolysis of 5-(β-methylmercaptoethyl)-hydantoin by reaction at elevated temperature and pressure in an aqueous alkaline medium. There are obtained alkali methioninate solutions from which there can be separated methionine.

16 Claims, No Drawings

PROCESS FOR THE HYDROLYSIS OF 5-(β-METHYLMERCAPTOETHYL)-HYDANTOIN

BACKGROUND OF THE INVENTION

The invention is directed to a process for the hydrolysis of 5-(β-methylmercaptoethyl)-hydantoin by hydrolysis at elevated temperature and elevated pressure in an alkaline aqueous medium from which methionine can be separated.

It has long been known to obtain methionine by hydrolysis of the corresponding hydantoin.

U.S. Pat. No. 2,527,366 is directed to the hydrolysis of 5-(β-methylmercaptoethyl)-hydantoin (in the following text called hydantoin (I)) in an aqueous barium hydroxide solution under pressure and elevated temperature. However, this process requires considerable amounts of expensive barium hydroxide. Experiments carried out under similar conditions with ammonium hydroxide or calcium hydroxide gave either poor yields or strongly colored products.

Furthermore, it is known from U.S. Pat. No. 2,557,920 to produce α-aminoacids by saponification of hydantoins using sodium hydroxide. According to this process, however, there are required at least 3 moles of sodium hydroxide per mole of hydantoin.

In U.S. Pat. No. 4,272,631 there is described the use of a mixture of alkali and alkaline earth hydroxides for the saponification of hydantoin (I). For the production of an alkaline methioninate solution first there must be removed by precipitation the alkaline earth ions present. Besides there are only obtained yields at a maximum of 80.5% of theory.

Employing a mixture of ammonium hydroxide and calcium hydroxide has been found completely unsatisfactory with a yield of 74%.

The process described in German AS No. 1518339 depends on the expectation that in the hydrolysis of hydantoins through removal of the gaseous reaction products ammonia and carbon dioxide the reaction equilibrium can be shifted in the direction of the formation of aminoacid and thus the yield increased.

However, to carry out the process there is required an expensive regulation of pressure which limits the pressure during the hydrolysis to a value which on the one hand is somewhat higher than the vapor pressure of water at the reaction temperature selected but on the other hand is below the theoretical autogeneously established pressure.

There has now been found a process for the hydrolysis of 5-(β-methylmercaptoethyl)-hydantoin which leads to increased yields in the presence of excess ammonia.

SUMMARY OF THE INVENTION

The invention is directed to a process for the hydrolysis of 5-(β-methylmercaptoethyl)-hydantoin at elevated temperature and elevated pressure in an aqueous alkaline medium characterized by carrying out the hydrolysis in a reaction solution containing 0.5 to 3 equivalents of at least one alkali hydroxide, carbonate, and/or bicarbonate based on the amount of hydantoin, in the presence of added, excess ammonia and in a given case, after conclusion of the hydrolysis methionine is separated off, if there is desired the solid aminoacid and not the intermediately produced alkali methioninate solution.

This means that in contrast to German AS No. 1518339 during the hydrolysis there is present in the reaction system not only the ammonia formed in the course of the reaction but there are also present further amounts of ammonia. This concerns both the gas space over the reaction solution and also the reaction solution itself.

The ammonia is added to the hydantoin (I) containing alkaline solution either entirely at the beginning of the hydrolysis or continuously or discontinuously during the course of the reaction and is added in gaseous form and/or as an aqueous, preferably concentrated, ammonium hydroxide solution in an amount that there is attained an excess of 0.5 to 25 equivalents, based on the amount of hydantoin (I). Excess means additional to the ammonia formed during the hydrolysis.

In a preferred process variant there is employed an excess of 1 to 15 equivalents of ammonia and 0.8 to 2 equivalents, especially 0.8 to 1.5 equivalents of at least one alkali hydroxide, alkali carbonate and/or alkali hydrogen carbonate.

1 equivalent of the alkali compounds is especially preferred because with this variant after driving off the ammonia and carbon dioxide with the known methods from the reaction solution resulting after conclusion of the hydrolysis there is obtained an alkali methioninate solution which is practically free from foreign salts and therefore is particularly well suited for supplementing animal feed. Methionine can also be precipitated and isolated from this solution in an advantageous manner by neutralization with an acid according to the state of the art. Thereby considerably lower amount of foreign salt must be separated than according to the previously known processes and the load on the waste water is reduced correspondingly.

Advantageous there are employed the following alkali compounds: sodium hydroxide, potassium hydroxide, sodium bicarbonate, potassium bicarbonate, sodium carbonate and potassium carbonate.

In a suitable illustrative form of the invention the hydrolysis is carried out, e.g. in an autoclave under the autogenous pressure estabished in each case, which is composed chiefly of the partial pressure of the steam, the carbon dioxide and ammonia formed in the reactions, as well as the excess ammonia, insofar as these gases are not dissolved in the reaction solution.

For carrying out the process continuously there are suited e.g. pressure resistant columns.

The hydrolysis is carried out preferably in a temperature range between 120° and 220° C., especially between 130° and 190° C. In the continuous method of operation the hydantoin containing reaction solution is led through a reaction zone during a time period which is sufficient to hydrolyze the hydantoin (I). A valuable variant of the process of the invention is to withdraw continuously or discontinuously, preferably continuously, from the gas space above the reaction solution the gaseous compounds carbon dioxide and ammonia formed during the hydrolysis and simultaneously at least compensating for the ammonia loss thereby occurring in the reaction system by adding corresponding amounts of ammonia in gaseous form or as ammonium hydroxide solution. Through this there is fulfilled the applicable prerequisite for the successful carrying out of the process of the invention, which must be carried out in an excess of ammonia during the hydrolysis.

The gases carbon dioxide and ammonia drawn off during or after the end of the hydrolysis can be recycled after working up by distillation. The hydantoin (I) employed in the process need not be a pure compound. For example there can be employed a hydantoin containing mixture which has been produced by reaction of 3-methylmercaptopropionaldehyde, ammonium bicarbonate and a cyanide compound in aqueous solution according to the state of the art.

In contrast to the processes according to the state of the art the process of the invention succeeds in increasing the yield by the addition of ammonia and suppressing the formation of byproducts.

This is particularly true if alkali compound and hydantoin (I) are employed in equivalent amounts.

Indeed in using alkali compounds in an equivalence <1 there also occurs the complete saponification of the hydantoin (I). However, corresponding to the deficiency of alkali it cannot form alkali methioninate to the same extent.

In this case a dimer of methionine is formed via a peptide coupling.

The desired concentration of alkali methioninate or the corresponding dimers for the later use can be established either through corresponding selection of the hydantoin (I) concentration or through dilution or concentration of the solutions resulting from the hydrolysis.

Methionine is isolated from the resulting hydrolysis with generally known procedures, which inter alia also can be taken from the publications mentioned as the state of the art.

The following examples explain the process of the invention. The amounts of methionine isolated in each case from the alkali methioninate solutions document the efficiency of the process of the invention.

The process can comprise, consist essentially of, or consist of the stated steps with the recited materials.

DETAILED DESCRIPTION

EXAMPLE 1

The solution of 60 grams of 5-($\beta$-methylmercaptoethyl)-hydantoin, corresponding to 0.34 mole, and 0.34 mole of sodium hydroxide in 220 ml of water was treated with 23 ml (0.34 mole) of concentrated ammonia solution and heated for 4 hours to 165° C. in a 500 ml stainless steel autoclave provided with a stirrer. After the end of the reaction under autogenous pressure the mixture was cooled and the pressure relieved. The yield of methionine from the sodium methioninate solution was 92.6%.

When the reaction is carried out under otherwise the same conditions but without addition of ammonia and the gaseous compounds formed in the reaction left in the autoclave, methionine is obtained in a yield of 75.8%.

EXAMPLE 2

The solution of 0.34 mole of 5-($\beta$-methylmercaptoethyl)-hydantoin and 0.34 mole of potassium hydroxide in 180 ml of water was treated with 5 moles of concentrated ammonia solution and heated for 4 hours at 160° C. in a 1000 ml autoclave. After the end of the reaction under autogenous pressure there was isolated methionine in 95.6% yield from the potasssium methioninate solution.

When the reaction is carried out under otherwise the same conditions but without addition of ammonia, methionine was formed in a yield of 71.1%.

EXAMPLE 3

The solution of 0.34 mole of 5-($\beta$-methylmercaptoethyl)-hydantoin and 0.34 mole of potassium bicarbonate in 200 ml of water were treated with 70 ml (1 mole) of concentrated ammonia solution and heated at 170° C. for 3 hours in an autoclave. After the customary working up methionine was obtained in 93.4% yield.

When the reaction is carried out under otherwise the same conditions but without addition of ammonia, methionine was formed in 74.3% yield.

EXAMPLE 4

The solution of 0.34 mole of 5-($\beta$-methylmercaptoethyl)-hydantoin and 0.51 mole of sodium hydroxide in 220 ml of water was treated with 1 mole of ammonia and heated for 4 hours at 160° C. in an autoclave. The methionine yield was 97.4%.

When the reaction was carried out under otherwise the same conditions but without addition of ammonia there was formed methionine in 84.8% yield.

EXAMPLE 5

There were added to crude 5-($\beta$-methylmercaptoethyl)-hydantoin which contained 0.34 ml of hydantoin and was produced according to customary process by reaction of 3-methylmercaptopropionaldehyde with ammonium bicarbonate and hydrocyanic acid, 0.34 mole of NaOH and 0.34 mole of concentrated ammonia solution. The mixture was filled up with water to about 320 ml and heated for 4 hours at 165° C. in an autoclave. The yield of methionine was 92.5%.

When the reaction was carried out under otherwise the same conditions but instead of ammonia under addition of 0.34 mole of ammonium bicarbonate the yield of methionine was 71.6%.

EXAMPLE 6

The solution of 0.34 mole of 5-($\beta$-methymercaptoethyl)-hydantoin and 0.31 mole of sodium hydroxide in 200 ml of water was treated with 115 ml (1.7 moles) of concentrated ammonia solution and heated for 4 hours at 160° C. in an autoclave. The yield of methionine was 76.0% besides a yield of 18.1% of methionine dimer (N-methionyl-methionine).

When the reaction was carried out under otherwise the same conditions but without addition of ammonia there was formed methionine in a yield of 64.5% besides a yield of 21% of methionine dimer (N-methionyl-methionine).

EXAMPLE 7

There were fed hourly to the head of a pressure resistant column a solution of 174.2 kg (1 k mole) of 5-($\beta$-methymercaptoethyl)-hydantoin in 260 l of water produced according to customary process as well as 80 kg of 50% (=1 kmole) sodium hydroxide. Simultaneously there was led into the lower part of the column 34.1 kg/h (2 kmole) of gaseous ammonia and a reaction temperature of 160° C. established. There were drawn off at the head of the column ammonia, carbon dioxide, and steam over a pressure resistant valve. The hydrolysate leaving the sump of the column was relieved of pressure and cooled. The yield of methionine was 97.0%.

When the continuous saponification was carried out under otherwise the same conditions but without introduction of ammonia then there was formed methionine in a yield of 81.2%.

The entire disclosure of German priority application P No. 3335218.6 is hereby incorporated by reference.

What is claimed is:

1. In a process for the hydrolysis of 5-(β-methylmercaptoethyl)-hydantoin at elevated temperature and pressure in an aqueous alkaline medium, the improvement comprising carrying out the hydrolysis in a reaction solution comtaining 0.5 to 3 equivalents of at least one alkali metal hydroxide, alkali metal carbonate, alkali metal hydrogen carbonate or a mixture thereof based on the amount of hydantoin in the presence of excess ammonia.

2. A process according to claim 1 wherein the alkali metal is sodium or potassium.

3. A process according to claim 1 including the step of separating off the methionine formed after the conclusion of the hydrolysis.

4. A process according to claim 1 wherein there is added to the reaction solution either at the beginning of the hydrolysis or continuously or discontinuously during the hydrolysis sufficient ammonia in gaseous form, as aqueous ammonium hydroxide solution or both in gaseous form and as aqueous ammonium hydroxide so that there is attained an excess of 0.5 to 25 equivalents of ammonia based on the amount of hydantoin.

5. A process according to claim 4 wherein there is employed an excess of 1–15 equivalents of ammonia, based on the amount of hydatoin.

6. A process according to claim 5 wherein there is employed 0.8–1.5 equivalents of the alkali metal hydroxide, carbonate or hydrogen carbonate, based on the amount of hydantoin.

7. A process according to claim 6 wherein there is employed 1 equivalent of the alkali metal hydroxide, carbonate or hydrogen carbonate, based on the amount of hydantoin.

8. A process according to claim 4 wherein the hydrolysis is carried out under autogenous pressure.

9. A process according to claim 1 wherein the hydrolysis is carried out under autogenous pressure.

10. A process according to claim 1 comprising at least partially separating the gaseous compounds formed in the reaction and simultaneously adding at least the amount of ammonia to make up for the ammonia lost thereby.

11. A process according to claim 1 wherein there is employed as starting material a hydantoin containing mixture which has been produced by reaction of 3-methylmercaptopropionaldehyde, ammonium bicarbonate and a cyanide compound.

12. A process according to claim 1 wherein after the end of the hydrolysis ammonia and carbon dioxide are separated from the hydrolysate.

13. A process according to claim 12 wherein there also are separated from the hydrolysate foreign salts.

14. A process according to claim 4 wherein all of the excess ammonia is added before the hydrolysis.

15. A process according to claim 4 wherein the excess ammonia is added continuously during the hydrolysis.

16. A process according to claim 4 wherein the excess ammonia is added discontinuously during the hydrolysis.

* * * * *